US010946088B2

(12) United States Patent
Haussmann et al.

(10) Patent No.: US 10,946,088 B2
(45) Date of Patent: Mar. 16, 2021

(54) PREPARATION OF INFLUENZA VIRUS VACCINE ANTIGENS

(71) Applicant: Seqirus UK Limited, Berkshire (GB)

(72) Inventors: Christoph Haussmann, Marburg (DE); Frank Hauschild, Marburg (DE); Bjorn Jobst, Marburg (DE)

(73) Assignee: Seqirus UK Limited, Berkshire (GB)

( * ) Notice: Subject to any disclaimer, the term of this patent is extended or adjusted under 35 U.S.C. 154(b) by 0 days.

(21) Appl. No.: 14/961,778

(22) Filed: Dec. 7, 2015

(65) Prior Publication Data

US 2016/0158341 A1 Jun. 9, 2016

Related U.S. Application Data

(63) Continuation of application No. 12/933,379, filed as application No. PCT/IB2009/005122 on Mar. 18, 2009, now abandoned.

(60) Provisional application No. 61/069,868, filed on Mar. 18, 2008.

(51) Int. Cl.
*C12N 7/02* (2006.01)
*A61K 39/145* (2006.01)
*C12N 7/00* (2006.01)
*A61K 39/12* (2006.01)
*A61K 39/00* (2006.01)

(52) U.S. Cl.
CPC ............ *A61K 39/145* (2013.01); *A61K 39/12* (2013.01); *C12N 7/00* (2013.01); *A61K 2039/5252* (2013.01); *C12N 2760/16034* (2013.01); *C12N 2760/16051* (2013.01); *C12N 2760/16134* (2013.01); *C12N 2760/16163* (2013.01)

(58) Field of Classification Search
CPC ........ A61K 39/145; A61K 39/12; C12N 7/00; C12N 7/02; C12N 2760/16111; C12N 2760/16051; A16K 39/16051
See application file for complete search history.

(56) References Cited

U.S. PATENT DOCUMENTS

| | | | |
|---|---|---|---|
| 4,064,232 A | 12/1977 | Bachmayer et al. | |
| 4,140,762 A | 2/1979 | Bachmayer et al. | |
| 4,158,054 A | 6/1979 | Furminger et al. | |
| 4,327,182 A | 4/1982 | Benedictus | |
| 5,948,410 A | 9/1999 | Van Scharrenburg et al. | |
| 6,048,537 A | 6/2000 | Violay et al. | |
| 7,238,349 B1 | 7/2007 | D'Hondt et al. | |
| 7,316,813 B2* | 1/2008 | Eichhorn | A61K 39/145 424/204.1 |
| 8,808,686 B2* | 8/2014 | Del Giudice | A61K 39/145 424/93.6 |
| 9,730,999 B2* | 8/2017 | Hanon | A61K 39/145 |
| 2007/0141078 A1 | 6/2007 | D'Hondt et al. | |
| 2008/0014217 A1 | 1/2008 | Hanon et al. | |
| 2009/0285854 A1 | 11/2009 | Contorni | |

FOREIGN PATENT DOCUMENTS

| | | |
|---|---|---|
| CN | 1911445 B | 4/2013 |
| EP | 1878424 A | 1/2008 |
| EP | 1930025 B1 | 5/2013 |
| GB | 1140316 | 1/1969 |
| WO | WO-94/19013 A | 9/1994 |
| WO | WO-00/35481 A | 6/2000 |
| WO | WO-01/21151 A1 | 3/2001 |
| WO | WO-01 /22992 A | 4/2001 |
| WO | WO-01 /38362 A | 5/2001 |
| WO | WO-01 /60402 A | 8/2001 |
| WO | WO-02/28422 A2 | 4/2002 |
| WO | WO-02/067983 A1 | 9/2002 |
| WO | WO-02/074336 A2 | 9/2002 |
| WO | WO-02/097072 A2 | 12/2002 |
| WO | WO-2005/113756 A1 | 12/2005 |
| WO | WO-2006/100110 A1 | 9/2006 |
| WO | WO-2007/018152 A1 | 2/2007 |
| WO | WO-2007/052056 A | 5/2007 |
| WO | WO-2007/052057 A2 | 5/2007 |
| WO | WO-2007/052059 A | 5/2007 |
| WO | WO-2007/052061 A | 5/2007 |
| WO | WO 2007/052163 A2 | 5/2007 |
| WO | WO-2008/009309 A1 | 1/2008 |

OTHER PUBLICATIONS

Wikipedia searched on Aug. 6, 2018, pagers 1-3.*
Hao et al. J. Pharm Sci. 2008, vol. 97 (12), pp. 5186-5197.*
Decision revoking European Patent No. 2,268,309, dated May 19, 2017, 2 pages.
Grounds for the decision revoking European Patent No. 2,268,309, dated May 19, 2017, 18 pages.
Experimental report, "The effect of salt concentration on antigen yield in vaccine production," submitted in European Patent No. 2,268,309 Opposition, 5 pages.
Declaration of Christopher Dadd, submitted in European Patent No. 2,268,309 Opposition, dated Mar. 18, 2017, 4 pages.
Declaration of Francesco Doro, submitted in European Patent No. 2,268,309 Opposition, dated Mar. 15, 2017, 8 pages.
Excerpts from Practical Immunology, Hudson and Hay, $2^{nd}$ ed., 1980, 3 pages.
Phosphate-buffered saline (PBS), Cold Spring Harbor Protocols, CSH protocols.cshlp.org, 2006, 1 page.
Furchgott et al., "Electrophoretic studies on human red blood cells," J. Gen. Physiol., 24:447-457 (1941).
Bateman et al., "The electrophoretic properties of red blood cells: the effect of changing pH and ionic strength," Archives of Biochem. Biophys., 60: 44-51 (1956).

(Continued)

Primary Examiner — Bao Q Li
(74) Attorney, Agent, or Firm — Finnegan, Henderson, Farabow, Garrett & Dunner LLP

(57) ABSTRACT

A number of improvements for preparing vaccine antigens from disintegrated influenza viruses are disclosed. A splitting step can be followed by detergent exchange. Splitting can take place in the presence of a buffer with a higher ionic strength and/or in the presence of phosphate buffer.

22 Claims, 1 Drawing Sheet

(56) References Cited

OTHER PUBLICATIONS

Kraft et al., "Parallel inhibition of active force and relaxed fiber stiffness by caldesmon fragments at physiological ionic strength and temperature conditions: additional evidence that weak cross-bridge binding to actin is an essential intermediate for force generation," Biophysical J., 68: 2404-2418 (1995).

Technical Information Plantacare® 2000 U P, 2013, 2 pages.

Declaration of Christopher Dadd (including 4 exhibits), submitted in European Patent No. 2,268,309 Opposition, dated Apr. 6, 2017, 19 pages.

PBS (Phosphate Buffered Salts) Tablets, from Takara Bio Inc., v201610, 2 pages.

Dulbecco et al., "One-step growth curve of western equine encephalomyelitis virus on chicken embryo cells grown in vitro and analysis of virus yields from single cells," J Exp. Med., 99(2): 183-199 (1954).

English translation of the Second Office Action, dated Dec. 21, 2012, for Chinese application No. 200980110089.4, filed on Mar. 18, 2009, 7 pages.

International Search Report dated Dec. 17, 2009, for PCT/IB2009/005122 filed Mar. 18, 2009, 6 pages.

Qi et al. (2004). "Development of Influenza Vaccines," China J. Biological, 17(3):190-192.

Belshe (2007). "Translational Research on Vaccines; Influenza as an example" Clinical Pharmacology & Therapeutics, 82(6):745-749.

Gerentes et al. (1996). "Simultaneous purification of influenza haemagglutinin and neuraminidase proteins by immunochromatography" J. Virol. Methods, 58:155-165.

Gross et al. (1981). "Comparison of new triton X-100- and tween-ether-treated split-treated vaccines in children," J. Clin. Microbiol., 14(5): 534-538.

Kelly et al. (2002). "Low-Conductivity Buffers for High-Sensitivity NMR Measurements" J. Am. Chem. Soc., 124:12013-12019.

Notice of Opposition filed by GlaxoSmithKline Biologicals S.A., mailed Oct. 21, 2015 against EP 2268309, 14 pages.

O'Hagan (2007). "MF59 is a safe and potent vaccine adjuvant that enhances protection against influenza virus infection" Expert Rev. Vaccines, 6(5):699-710.

Sambrook et al. (1989). "Molecular Cloning: A Laboratory Manual", 2nd Edition, Table B.7.

Stein et al. (1979). "Acidic polypeptides can assemble both histones and chromatin in vitro at physiological ionic strength" Proc. Natl Acad. Sci, USA 76(10):5000-5004.

Supplemental Data, "The effect of buffer types on antigen recovery in vaccine production," submitted on Oct. 3, 2011, filed in relation to EP2268309, 1 page.

Extended European Search Report, issued in European Patent Application No. 18203041.1, dated Feb. 21, 2019, 9 pages.

Kalbfuss B. et al., "Harvesting and Concentration of Human Influenza A Virus Produced in Serum-Free Mammalian Cell Culture for the Production of Vaccines," Biotech. & Bioeng., 97:73-85 (2007).

Wickramasinghe S.R. et al., "Tangential Flow Microfiltration and Ultrafiltration for Human Influenza A Virus Concentration and Purification," Biotech. & Bioeng., 92:199-208 (2005).

Otto, K. et al., "Effect of Ionic Strength on Initial Interactions of *Escherichia coli* with Surfaces, Studied On-Line by a Novel Quartz Crystal Microbalance Technique," *J. Bacteriology*, 181:5210-5218 (1999).

\* cited by examiner

PREPARATION OF INFLUENZA VIRUS VACCINE ANTIGENS

RELATED APPLICATIONS

This application is a Continuation of U.S. patent application Ser. No. 12/933,379, with an international filing date of Mar. 18, 2009, which is the U.S. National Stage of International Patent Application No. PCT/IB2009/005122, filed Mar. 18, 2009, which claims the benefit under 35 U.S.C. § 119(e) of U.S. Provisional Application No. 61/069,868, the disclosures of which are herein incorporated by reference in their entirety.

All documents cited herein are hereby incorporated by reference in their entirety.

TECHNICAL FIELD

This invention is in the field of influenza vaccine preparation.

BACKGROUND ART

Influenza vaccines currently in general use are described in chapters 17 & 18 of reference 1. They are based on live virus or inactivated virus, and inactivated vaccines can be based on whole virus, "split" virus or on purified surface antigens (including hemagglutinin and also, usually, neuraminidase).

A variety of different procedures are known for preparing both split and surface antigen vaccines. For example, various splitting procedures are disclosed in references 2-8, and different methods for preparing surface antigen vaccines are disclosed in references 9-14.

It is an object of the invention to provide further and improved methods for preparing split and surface antigen vaccines.

DISCLOSURE OF THE INVENTION

The inventor has devised a number of improvements to existing processes for preparing vaccine antigens from disintegrated influenza viruses.

Modified Timing of Detergent Use

In an existing purification process, influenza virions are exposed to a first detergent (e.g. a polysorbate, such as polysorbate 80) prior to splitting by a second detergent (e.g. CTAB). The first detergent is used prior to virus inactivation, whereas the second detergent is added after inactivation. The second detergent is removed later in the process, but the first detergent remains, thereby facilitating antigen solubility. In contrast, according to a first aspect of the present invention the first detergent is used later in the process, and in particular after the second detergent has already been used for splitting virions. This change in timing and order has been associated with a >20-fold increase in antigen yield, in particular with a H5 subtype influenza A virus.

Thus the invention provides a process for disrupting influenza v1nons, comprising steps of: (i) obtaining a composition comprising influenza virions in the absence of detergent; (ii) inactivating the influenza virions in the absence of detergent; (iii) splitting the inactivated virions with a reagent comprising a first detergent; and (iv) exchanging the first detergent for a second detergent. The detergent exchange step may occur any time after the splitting step, but ideally occurs prior to a step of virion capture e.g. by a process selected from affinity capture, pseudo-affinity capture, chromatography or adsorption (see below). Thus the second detergent may be added after splitting but before virion capture. Further quantities of the second detergent may be added after virion capture, particularly if the amount of second detergent previously added was less than 1.5 g/L.

Disrupted virions obtained by this process can be used for the preparation of influenza vaccines.

The invention also provides, in a process for disrupting influenza virions, the improvements consisting of: inactivating influenza virions in the absence of detergent; splitting the inactivated virions with a reagent comprising a first detergent; and exchanging the first detergent for a second detergent after splitting.

In alternative embodiments of the first aspect, the second detergent is added after inactivation but before splitting. Thus the invention provides a process for disrupting influenza virions, comprising steps of: (i) obtaining a composition comprising influenza virions in the absence of detergent; (ii) inactivating the influenza virions in the absence of detergent; (iii) adding a second detergent without splitting the inactivated virions; (iv) splitting the inactivated virions in the presence of the second detergent with a reagent comprising a first detergent; and (v) removing the first detergent while retaining the second detergent.

Disrupted virions obtained by this process can be used for the preparation of influenza vaccines.

The invention also provides, in a process for disrupting influenza virions, the improvements consisting of: inactivating influenza virions in the absence of detergent; splitting the inactivated virions with a reagent comprising a first detergent, in the presence of a second detergent; and removing the first detergent after splitting while retaining the second detergent.

In a further alternative embodiment with modified timing of detergent use, a detergent is added prior to virion inactivation, but after an ultrafiltration/diafiltration step performed on virions. Thus the invention provides a process for disrupting influenza virions, comprising steps of: (i) obtaining a composition comprising influenza virions in the absence of detergent; (ii) performing ultrafiltration/diafiltration on the virion-containing composition; (iii) adding a detergent to the filtered virion-containing composition without splitting the virions; and (iv) inactivating the influenza virions. The process may include a further step of (v) splitting the inactivated virions with a detergent. The detergent used in step (v) may be different from the detergent used in step (iii). Further quantities of the same detergent which was used in step (iii) may be added after step (v), particularly if the amount of detergent added in step (iii) was less than 1.5 g/L.

In embodiments where further quantities of detergent are added when the previously-added amount was less than 1.5 g/L, the further addition may take place prior to a further ultrafiltration/diafiltration step.

Improved Splitting Procedure

Splitting procedures for influenza vaccines involve the treatment of virions with solubilising concentrations of detergents. Suitable detergents include the polysorbates (Tweens) [6], Triton X-100 [6,10,15], cetyl trimethyl ammonium bromide (CTAB) [9,16], and deoxycholate [2,17].

In an existing purification process, influenza virions are split by exposure to detergent in the presence of 20 mM Tris/HCl. In contrast, according to a second aspect of the present invention the detergent is used in the presence of a buffer with a higher ionic strength. Thus the invention provides a process for disrupting influenza virions, comprising steps of: (i) obtaining a composition comprising influenza virions; (ii) splitting the virions by exposure to a detergent in a buffer having an ionic strength of 100 mM or greater. This increased ionic strength has been associated with a >20-fold increase in antigen yield, in particular with a H5 subtype influenza A virus.

Disrupted virions obtained by this process can be used for the preparation of influenza vaccines.

Useful buffers have an ionic strength of at least 100 mM e.g. ≥200 mM, ≥300 mM, ≥400 mM, ≥500 mM, ≥600 mM, ≥700 mM, ≥800 mM, etc. This higher ionic strength can be achieved in various ways e.g. by using monovalent ions (e.g. NaCl), divalent ions (e.g. sulphates), trivalent ions (e.g. phosphates), etc. The use of trivalent ions is a convenient way of increasing ionic strength. One suitable buffer, particularly when used in a CTAB-based splitting procedure, includes 200 mM NaCl in a 50 mM phosphate buffer, pH 7.5. Care should be taken when increasing the ionic strength during splitting, particularly for viruses grown in cell culture, so as to avoid the solubilisation of high amounts of DNA that will then be retained during further processing steps.

The invention also provides, in a process for disrupting influenza virions, the improvements consisting of: splitting virions using a detergent in a buffer having an ionic strength of 100 mM or greater.

Phosphate Buffer

In an existing purification process, influenza virions are maintained before, during and after splitting in a Tris buffer. In contrast, according to a third aspect of the present invention the virions are maintained before, during and after splitting in a phosphate buffer. This buffer change has been associated with a >20-fold increase in antigen yield, in particular with a H5 subtype influenza A virus.

Thus the invention provides a process for disrupting influenza virions, comprising steps of: (i) obtaining a composition comprising influenza virions in the presence of a phosphate buffer, (ii) inactivating the influenza virions in the presence of a phosphate buffer; and (iii) splitting the inactivated virions in the presence of a phosphate buffer.

Disrupted virions obtained by this process can be used for the preparation of influenza vaccines.

Useful phosphate buffers have a pH between 6.5 and 8.5 e.g. between 7.0 and 8.0, or about 7.5.

The invention also provides, in a process for disrupting influenza virions, the improvement consisting of: inactivating and then splitting virions both in the presence of a phosphate buffer.

Ultrafiltration Membrane

In an existing purification process, semi-purified post-splitting influenza surface antigens are further purified by ultrafiltration/diafiltration through a polyethersulfone (PES) membrane. In contrast, according to a fourth aspect of the present invention the ultrafiltration uses a cellulose membrane. This membrane change, which reduces hydrophobicity and protein retention, has been associated with a >20-fold increase in antigen yield, in particular with a H5 subtype influenza A virus.

Thus the invention provides a process for purifying influenza virus surface glycoproteins from a mixture comprising said glycoproteins, comprising a step of ultrafiltering said mixture through a cellulose membrane. Purified glycoproteins obtained by this process can be used for the preparation of influenza vaccines.

The invention also provides, in a process for purifying influenza virus surface glycoproteins from a mixture comprising said glycoproteins by ultrafiltration, the improvement consisting of using a cellulose ultrafiltration membrane.

Various types of cellulose membrane can be used. These can be based on cellulose itself, cellulose esters (e.g. a diacetate, a triacetate, a nitrate, etc.), or mixtures thereof. For instance, reference 18 discloses membranes having a non-fibrous polymeric microporous base with a membrane layer formed from cellulose and/or cellulose acetate. The membrane layer can have a thickness between 1 and 20 μm and can extend into the microporous base by between 5-30 μm. Reference 19 discloses asymmetrical ultrafiltration membranes based on cellulose triacetate, optionally substituted by up to 30% cellulose diacetate. Reference 20 discloses diafiltration membranes in the form of a hollow fiber with a continuous internal cavity made of cellulose acetate or a cellulose acetate derivative.

Introduction of an Additional Process Step Prior to the First Chromatography Step To separate influenza virions from cell culture fermentation medium components in an existing purification process, influenza virions are captured from the culture harvest on a resin. It has been observed that binding to the resin is incomplete for some strains.

According to a fourth aspect of the present invention, prior to the capture step the virus harvest is subjected to an ultra-/diafiltration step into a low conductivity buffer. This initial step can result in up to a 10-fold increase of antigen yield depending on the influenza virus strain, and is particularly useful for virions that do not bind to the capture agent.

Thus the invention provides a process for treating a liquid medium containing influenza virions, comprising a step of diafiltration of the liquid medium to provide a virion-containing retentate including a low conductivity buffer. The retentate can then be treated further e.g. by affinity capture, adsorption, chromatography, etc.

The invention also provides, in a process for separating influenza virions from a liquid medium containing them, the improvement consisting of diafiltering the liquid medium to provide a virion-containing retentate including a low conductivity buffer, prior to separation.

The invention also provides a process for separating influenza virions from a liquid medium containing the virions, comprising steps of: (i) diafiltration of the liquid medium to provide a virion-containing retentate including a low conductivity buffer; and then (ii) capturing virions from the retentate by a process selected from affinity capture, pseudo-affinity capture, chromatography or adsorption.

Retentates and virions obtained by these processes can be used for preparation of influenza vaccines.

Diafiltration utilizes permeable membrane filters to separate the components of solutions and suspensions based on their molecular size. Small components can pass through the membrane to form a filtrate, whereas larger components (e.g. virions) cannot, and so are retained. Diafiltration can be used to reduce the concentration of salts, solvents, or other low molecular weight species in a liquid medium, and optionally to introduce new species (e.g. to exchange buffers). Diafiltration can be either continuous or discontinuous. Continuous diafiltration involves washing out original low molecular weight species by adding water or buffer to the sample at substantially the same rate as filtrate is being generated. If a buffer is used for diafiltration then the concentration of the new buffer salt in the sample increases at a rate inversely proportional to that of the species being removed. Using continuous diafiltration, greater than 99.5% of a 100% permeable solute can typically be removed by washing through six equivalent sample volumes with the buffer of choice. Discontinuous diafiltration dilutes a sample with an volume of water or buffer and then concentrates back to the original volume. Continuous diafiltration is preferred with the present invention. Typically diafiltration of the medium will involve at least two (e.g. 3, 4, 5, 6, 7, 8, 9, 10 or more) diafiltration volumes (i.e. at least 2× the volume of the sample at the start of diafiltration).

The diafiltration can use any suitable membrane (e.g. PES, celluloses, etc. as discussed above) in any suitable form (e.g. hollow fire, cassette, spirals, etc.). The membrane will have a cut-off limit that retains virions e.g. 500 kDa.

The diafiltration step may be preceded by an ultrafiltration step e.g. to concentrate the liquid medium. Such a concentration will usually be at least a 2-fold concentration e.g. >2-fold, >3-fold, >4-fold, >5-fold, >10-fold, etc. The ultrafiltration/concentration and the subsequent diafiltration can be performed using the same apparatus. Concentration prior to diafiltration is advantageous as it reduces the volume of liquid required for completing diafiltration.

After diafiltration, the retentate includes a low conductivity buffer. Suitable buffers include phosphate buffers, Tris/HCl buffers, TES buffers, citrate buffers, borate buffers, acetate buffers, glycine buffers etc. The retentate will typically have a conductivity of less than 20 mS/cm e.g. between 0.5-10 mS/cm, or between 1.0-1.4 mS/cm. A 10 mM phosphate buffer is suitable.

Capturing virions from the diafiltration retentate can use affinity capture, pseudo-affinity capture, chromatography or adsorption. Suitable techniques are known for influenza viruses. For example, affinity or pseudo-affinity capture is known using *Euonymus europaeus* lectin [21], or using Cellufine Sulfate (CS) or sulfated Sephadex columns. Adsorption can be used e.g. to polyelectrolytes [22], to barium sulfate [23], to a calcium phosphate salt [24], etc. Usefully, prior to its use the capture material will be equilibrated with the low conductivity buffer present in the retentate. Thus, for instance, a capture resin can be equilibrated with 10 m M phosphate buffer. The same buffer can also be used for washing the capture material prior to release of captured virions.

Influenza Viruses

The invention may be used when preparing antigens from any suitable influenza virus, including influenza A, B and C viruses. It is particularly useful for use with strains of influenza A virus that can infect humans.

Influenza virus strains for use in vaccines change from season to season. In the current inter-pandemic period, vaccines typically include two influenza A strains (H1N1 and H3N2) and one influenza B strain, and trivalent vaccines are typical. The invention can be used with such inter-pandemic viruses, but may also be used with viruses from pandemic strains (i.e. strains to which the vaccine recipient and the general human population are immunologically naïve), in particular of influenza A virus. Thus the invention may be used with any of influenza A virus hemagglutinin subtypes H1, H2, H3, H4, H5, H6, H7, H8, H9, H10, H11, H12, H13, H14, H15 or H16. The virus may additionally have any of NA subtypes N1, N2, N3, N4, N5, N6, N7, N8 or N9.

The invention is particularly useful with pandemic influenza A virus strains, such as H5N1 strains. Characteristics of a pandemic strain are: (a) it contains a new hemagglutinin compared to the hemagglutinins in currently-circulating human strains, i.e. one that has not been evident in the human population for over a decade (e.g. H2), or has not previously been seen at all in the human population (e.g. H5, H6 or H9, that have generally been found only in bird populations), such that the vaccine recipient and the general human population are immunologically naïve to the strain's hemagglutinin; (b) it is capable of being transmitted horizontally in the human population; and (c) it is pathogenic to humans. Pandemic strains H2, H5, H7 or H9 subtype strains e.g. H5N1, H5N3, H9N2, H2N2, H7N1 and H7N7 strains. Within the H5 subtype, a virus may fall into a number of clades e.g. clade 1 or clade 2. Six sub-clades of clade 2 have been identified with sub-clades 1, 2 and 3 having a distinct geographic distribution and are particularly relevant due to their implication in human infections.

Influenza B virus currently does not display different HA subtypes, but influenza B virus strains do fall into two distinct lineages. These lineages emerged in the late 1980s and have HAs which can be antigenically and/or genetically distinguished from each other [25]. Current influenza B virus strains are either B/Victoria/2/87-like or B/Yamagata/16/88-like. These strains are usually distinguished antigenically, but differences in amino acid sequences have also been described for distinguishing the two lineages e.g. B/Yamagata/16/88-like strains often (but not always) have HA proteins with deletions at amino acid residue 164, numbered relative to the 'Lee40' HA sequence [26]. The invention can be used with antigens from a B virus of either lineage.

The influenza virus may be attenuated. The influenza virus may be temperature-sensitive. The influenza virus may be cold-adapted. However, these three features are more typical when preparing live virus as a vaccine antigen.

The influenza virus may be resistant to antiviral therapy (e.g. resistant to oseltamivir [27] and/or zanamivir), including resistant pandemic strains [28].

An influenza virus used with the invention may be a reassortant strain, and may have been obtained by reverse genetics techniques. Reverse genetics techniques [e.g. 29-33] allow influenza viruses with desired genome segments to be prepared in vitro using plasmids. Typically, it involves expressing (a) DNA molecules that encode desired viral RNA molecules e.g. from poll promoters or bacteriophage RNA polymerase promoters, and (b) DNA molecules that encode viral proteins e.g. from poll promoters, such that expression of both types of DNA in a cell leads to assembly of a complete intact infectious virion. The DNA preferably provides all of the viral RNA and proteins, but it is also possible to use a helper virus to provide some of the RNA and proteins.

Plasmid-based methods using separate plasmids for producing each viral RNA can be used [34-36], and these methods will also involve the use of plasmids to express all or some (e.g. just the PB1, PB2, PA and NP proteins) of the viral proteins, with up to 12 plasmids being used in some methods. To reduce the number of plasmids needed, a recent approach [37] combines a plurality of RNA polymerase I transcription cassettes (for viral RNA synthesis) on the same plasmid (e.g. sequences encoding 1, 2, 3, 4, 5, 6, 7 or all 8 influenza A vRNA segments), and a plurality of protein-coding regions with RNA polymerase II promoters on another plasmid (e.g. sequences encoding 1, 2, 3, 4, 5, 6, 7 or all 8 influenza A mRNA transcripts). Preferred aspects of the reference 37 method involve: (a) PB1, PB2 and PA mRNA-encoding regions on a single plasmid; and (b) all 8 vRNA-encoding segments on a single plasmid. Including the NA and HA segments on one plasmid and the six other segments on another plasmid can also facilitate matters.

Poll promoters tend to be species-specific, and so the promoter may be chosen to match the cell type in which reverse genetics takes place e.g. in canine cells it is preferred to use a canine polI promoter [38,39]. As an alternative to using polI promoters to encode the viral RNA segments, however, it is possible to use bacteriophage polymerase promoters [40]. For instance, promoters for the SP6, T3 or T7 polymerases can conveniently be used. Because of the species-specificity of polI promoters then bacteriophage promoters can be more convenient for some cell types, although a cell must also be transfected with a plasmid encoding the exogenous polymerase enzyme.

In other techniques it is possible to use dual polI and polII promoters to simultaneously code for the viral RNAs and for expressible mRNAs from a single template [41,42].

Thus an influenza A virus may include one or more RNA segments from a A/PR/8/34 virus (typically 6 segments from A/PR/8/34, with the HA and N segments being from a vaccine strain, i.e. a 6:2 reassortant). It may also include one or more RNA segments from a A/WSN/33 virus, or from any other virus strain useful for generating reassortant viruses for vaccine preparation. An influenza A virus may include fewer than 6 (i.e. 0, 1, 2, 3, 4 or 5) viral segments from an AA/6/60 influenza virus (A/Ann Arbor/6/60). An influenza B virus may include fewer than 6 (i.e. 0, 1, 2, 3, 4 or 5) viral segments from an AA/1/66 influenza virus (B/Ann Arbor/1/66). Typically, the invention protects against a strain that is capable of human-to-human transmission, and so the strain's genome will usually include at least one RNA segment that originated in a mammalian (e.g. in a human) influenza virus. It may include NS segment that originated in an avian influenza virus.

Influenza Virus Growth and Virion Purification

Processes of the invention may be performed on a starting material containing influenza virions. These virions may be the product of virus growth either in eggs (e.g. specific pathogen free eggs) or in cell culture. The current standard method for influenza virus growth uses embryonated hen eggs, with virus being purified from the egg contents (allantoic fluid). More recently, however, viruses have been grown in animal cell culture and, for reasons of speed and patient allergies, this growth method is preferred.

A cell line used to grow influenza virus will typically be of mammalian origin. Suitable mammalian cells of origin include, but are not limited to, hamster, cattle, primate (including humans and monkeys) and dog cells, although the use of primate cells is not preferred. Various cell types may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line [43-45]. Suitable dog cells are e.g. kidney cells, as in the CLDK and MDCK cell lines.

Thus suitable cell lines include, but are not limited to: MDCK; CHO; CLDK; HKCC; 293T; BHK; Vero; MRC-5; PER.C6 [46]; FRhL2; WI-38; etc. Suitable cell lines are widely available e.g. from the American Type Cell Culture (ATCC) collection [47], from the Coriell Cell Repositories [48], or from the European Collection of Cell Cultures (ECACC). For example, the ATCC supplies various different Vero cells under catalog numbers CCL-81, CCL-81.2, CRL-1586 and CRL-1587, and it supplies MDCK cells under catalog number CCL-34. PER.C6 is available from the ECACC under deposit number 96022940.

The most preferred cell lines are those with mammalian-type glycosylation. As a less-preferred alternative to mammalian cell lines, virus can be grown on avian cell lines [e.g. refs. 49-51], including cell lines derived from ducks (e.g. duck retina) or hens. Examples of avian cell lines include avian embryonic stem cells [49,52] and duck retina cells [50]. Suitable avian embryonic stem cells, include the EBx cell line derived from chicken embryonic stem cells, EB45, EB14, and EB14-074 [53]. Chicken embryo fibroblasts (CEF) may also be used. Rather than using avian cells, however, the use of mammalian cells means that vaccines can be free from avian DNA and egg proteins (such as ovalbumin and ovomucoid), thereby reducing allergenicity.

The most preferred cell lines for growing influenza viruses are MDCK cell lines [54-57], derived from Madin Darby canine kidney. The original MDCK cell line is available from the ATCC as CCL-34, but derivatives of this cell line may also be used. For instance, reference 54 discloses a MDCK cell line that was adapted for growth in suspension culture ('MDCK 33016', deposited as DSM ACC 2219). Similarly, reference 58 discloses a MDCK-derived cell line that grows in suspension in serum-free culture ('B-702', deposited as FERM BP-7449). Reference 59 discloses non-tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (PTA-6503). Reference 60 discloses MDCK cell lines with high susceptibility to infection, including 'MDCK.5F1' cells (ATCC CRL-12042). Any of these MDCK cell lines can be used.

Virus may be grown on cells in adherent culture or in suspension. Microcarrier cultures can also be used. In some embodiments, the cells may thus be adapted for growth in suspension.

Cell lines are preferably grown in serum-free culture media and/or protein free media. A medium is referred to as a serum-free medium in the context of the present invention in which there are no additives from serum of human or animal origin. The cells growing in such cultures naturally contain proteins themselves, but a protein-free medium is understood to mean one in which multiplication of the cells occurs with exclusion of proteins, growth factors, other protein additives and non-serum proteins, but can optionally include proteins such as trypsin or other proteases that may be necessary for viral growth.

Cell lines supporting influenza virus replication are preferably grown below 37° C. [61](e.g. 30-36° C., or at about 30° C., 31° C., 32° C., 33° C., 34° C., 35° C., 36° C.) during viral replication.

Methods for propagating influenza virus in cultured cells generally includes the steps of inoculating a culture of cells with an inoculum of the strain to be grown, cultivating the infected cells for a desired time period for virus propagation, such as for example as determined by virus titer or antigen expression (e.g. between 24 and 168 hours after inoculation) and collecting the propagated virus. The cultured cells are inoculated with a virus (measured by PFU or $TCID_{50}$) to cell ratio of 1:500 to 1:1, preferably 1:100 to 1:5, more preferably 1:50 to 1:10. The virus is added to a suspension of the cells or is applied to a monolayer of the cells, and the virus is absorbed on the cells for at least 60 minutes but usually less than 300 minutes, preferably between 90 and 240 minutes at 25° C. to 40° C., preferably 28° C. to 37° C. The infected cell culture (e.g. monolayers) may be removed either by freeze-thawing or by enzymatic action to increase the viral content of the harvested culture supernatants. The harvested fluids are then either inactivated or stored frozen. Cultured cells may be infected at a multiplicity of infection ("m.o.i.") of about 0.0001 to 10, preferably 0.002 to 5, more preferably to 0.001 to 2. Still more preferably, the cells are infected at a m.o.i of about 0.01. Infected cells may be harvested 30 to 60 hours post infection. Preferably, the cells are harvested 34 to 48 hours post infection. Still more preferably, the cells are harvested 38 to 40 hours post infection. Proteases (typically trypsin) are generally added during cell culture to allow viral release, and the proteases can be added at any suitable stage during the culture e.g. before inoculation, at the same time as inoculation, or after inoculation [61].

In preferred embodiments, particularly with MDCK cells, a cell line is not passaged from the master working cell bank beyond 40 population-doubling levels.

The viral inoculum and the viral culture are preferably free from (i.e. will have been tested for and given a negative result for contamination by) herpes simplex virus, respiratory syncytial virus, parainfluenza virus 3, SARS coronavirus, adenovirus, rhinovirus, reoviruses, polyomaviruses, birnaviruses, circoviruses, and/or parvoviruses [62]. Absence of herpes simplex viruses is particularly preferred.

After growth of influenza virus, either in eggs or in cell culture, a virion-containing fluid will be available. The invention can be used to prepare antigens from such fluids, and a typical first step will be to purify (or concentrate) the virions from the fluid. This purification can be achieved by various methods [63,64]. For example, zonal centrifugation [65] may be used e.g. using a linear sucrose gradient solution. Density gradient centrifugation can use rate zonal or continuous-flow rotors [66]. Precipitation methods can also be used e.g. using polyethylene glycol [67]. Affinity or pseudo-affinity capture can be used, e.g. as described above (fifth aspect of the invention). Prior to such purification methods a virion-containing fluid may be subjected to filtration (e.g. to remove cellular debris) and/or ultrafiltration (typically with a large molecular weight cut-off e.g. ≥300 kDa, ≥500 kDa, or more) and/or diafiltration (as described above for the fifth aspect of the invention).

Virus Inactivation

Processes of the invention will typically include a step in which viruses are inactivated to remove their infectivity. Chemical means for inactivating a virus include treatment with an effective amount of one or more of the following agents: detergents, formaldehyde (e.g. as formalin), β-propiolactone, methylene blue, psoralen, carboxyfullerene (C60) or a combination of any thereof. Other methods of viral inactivation are known in the art, such as for example binary ethylamine, acetyl ethyleneimine, or gamma irradiation, or UV light.

Treatment with β-propiolactone is particularly useful, as disclosed in reference 68. In some embodiments of the invention the β-propiolactone may be present in a phosphate buffer.

In the step that precedes inactivation, virions will usually be concentrated as described above.

Splitting

Split virions are obtained by treating purified virions with detergents (ionic or non-ionic) and/or solvents to produce subvirion preparations. As mentioned above, methods of splitting influenza viruses are well known in the art, including the 'Tween-ether' method. Splitting is typically carried out on whole virions, which may be infectious or non-infectious. The disruption results in a full or partial solubilisation of the virus proteins, altering the integrity of the virus. The BEGRIVAC™, FLUARIX™, FLUZONE™ and FLUSHIELD™ products are split vaccines.

Suitable splitting agents include, but are not limited to: ethyl ether, polysorbate 80, deoxycholate, tri-N-butyl phosphate, alkylglycosides, alkylthioglycosides, acyl sugars, sulphobetaines, betaines, polyoxyethylenealkylethers, N,N-dialkyl-Glucamides, Hecameg, alkylphenoxy-polyethoxyethanols, quaternary ammonium compounds, sarcosyl, cetyl trimethyl ammonium bromides (e.g. Cetavlon™), tri-N-butyl phosphate, myristyltrimethylammonium salts, lipofectin, lipofectamine, and DOT-MA, the octyl- or nonylphenoxy polyoxyethanols (e.g. the Triton surfactants, such as Triton X-100 or Triton N101), nonoxynol 9 (NP9) Sympatens-NP/090,) polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g. in a sucrose density gradient solution).

Preferred splitting agents are ionic (e.g. cationic) detergents, such as cetyl trimethyl ammonium bromide (CTAB).

Splitting may take place in the presence of a buffer, such as a phosphate buffer. The buffer may usefully have a slightly acidic pH e.g. between 7.1 and 9.0, between 7.2 and 8.0, or about 7.5.

Splitting will usually take place in an aqueous solution, such as a buffered aqueous solution. As mentioned above, the solution may have an ionic strength of 100 mM or greater e.g. ≥200 mM, ≥300 mM, ≥400 mM, ≥500 mM, ≥600 mM, ≥700 mM, ≥800 mM, etc.

Detergent Exchange

After a splitting step it is common for the splitting detergent to be removed by adsorption. For instance, reference 14 reports that Amberlite XAD-4 (a macroreticular cross-linked aromatic polymer) is added after a CTAB/Tween splitting step in order to remove the detergents. The polymer is then itself removed by filtration.

In some circumstances it is desirable for detergent to remain in a final pharmaceutical formulation e.g. to solubilise certain active ingredients. In this case, previous processes for preparing influenza antigens from virions have added a non-ionic detergent (e.g. a polysorbate) prior to or with an ionic detergent splitting agent (e.g. CTAB). The ionic detergent is then fully removed (e.g. by Amberlite adsorption), but non-ionic detergent is left behind for solubilisation purposes. The non-ionic detergent may also be used to solubilise antigens so that they are not adsorbed during removal of the ionic detergent e.g. to ensure that Amberlite adsorption removes CTAB and not hemagglutinin.

A problem with this approach is that it is very difficult to achieve a desired final concentration of non-ionic detergent, because the amount of non-ionic detergent that remains in solution after splitting depends on the amount of protein, lipid, etc. that is present before the splitting step: a low level of input material will lead to a higher residual concentration of the non-ionic detergent, and vice versa.

To avoid this problem, in some embodiments of the invention virions are not exposed to detergent prior to the splitting step. Splitting exposes the virions to a first detergent (e.g. an ionic detergent, such as CTAB) at a desired concentration. The first detergent is then removed, but is replaced by a second detergent (e.g. a non-ionic detergent, such as polysorbate 80) i.e. the first detergent is exchanged for the second detergent. This step may involve: concurrent removal of the first detergent and addition of the second detergent; addition of the second detergent and subsequent removal of the first detergent; or removal of the first detergent and subsequent addition of the second detergent. The amount of second detergent that is present after the exchange may be lower, higher or equal to the amount of first detergent that was present before the exchange. Importantly, though, the concentration of the second detergent that remains after this step can be controlled and defined (e.g. relative to the amount of influenza antigen), whereas earlier addition of the second detergent can result in variable amounts of it remaining after the splitting detergent is removed.

Detergent exchange does not have to happen immediately after splitting. For instance, it is possible for further antigen purification to occur after splitting but prior to detergent exchange e.g. surface antigens can be purified from the split virions (see below) prior to the exchange.

Further Treatment of Split Virions

The invention provides various improvements in influenza virus splitting procedures, and so can be used in the production of split virus vaccines. In addition, however, split virions that are prepared according to the invention can be further treated so as to provide e.g. purified influenza virus surface antigens (haemagglutinin and, typically, also neuraminidase). As mentioned above, processes for preparing vaccines of this type are well known in the art, and the FLUVIRIN™, AGRIPPAL™ and INFLUVAC™ products are such vaccines. For example, ultracentrifugation of split virions can be used to prepare purified surface antigens. Similarly, zonal gradient centrifugation of split virions can be used (see example 1 of reference 9).

Thus a process of the invention for disrupting influenza virions can be used as part of an overall process for preparing a split virus vaccine or for preparing a purified surface antigen vaccine. In this process a hemagglutinin-containing antigen preparation will be obtained from a virus by a process in which influenza virions are disrupted by a process as described herein. The hemagglutinin-containing antigen preparation will then be used to prepare the vaccine, also as described herein.

HA is the main immunogen in current inactivated influenza vaccines, and vaccine doses are standardised by reference to HA levels, typically measured by SRID. Existing vaccines typically contain about 15 μg of HA per strain, although lower doses can be used e.g. for children, or in pandemic situations, or when using an adjuvant. Fractional doses such as ½ (i.e. 7.5 μg HA per strain), ¼ and ⅛ have been used, as have higher doses (e.g. 3× or 9× doses [69,70]). Thus vaccines may include between 0.1 and 150 μg of HA per influenza strain, preferably between 0.1 and 50 μg e.g. 0.1-20 μg, 0.1-15 μg, 0.1-10 μg, 0.1-7.5 μg, 0.5-5τg, etc. Particular doses include e.g. about 45, about 30, about 15, about 10, about 7.5, about 5, about 3.8, about 1.9, about 1.5, etc. per strain. A dose of 7.5 μg per strain is ideal for use in children.

A vaccine may include antigen(s) from one or more (e.g. 1, 2, 3, 4 or more) influenza virus strains, including influenza A virus and/or influenza B virus. Where a vaccine includes more than one strain of influenza, the different strains are typically grown separately and are mixed after the viruses have been harvested and antigens have been prepared. For a vaccine that contains antigen from more than one strain of influenza then a process of the invention may be used during preparation of a monovalent bulk antigen, and multiple monovalent bulks may then be mixed to prepare a multivalent vaccine. Thus a process of the invention may include the step of mixing antigens (hemagglutinin-containing antigen preparations) from more than one influenza strain.

HA used with the invention may be a natural HA as found in a virus, or may have been modified. For instance, it is known to modify HA to remove determinants (e.g. hyper-basic regions around the cleavage site between HA1 and HA2) that cause a virus to be highly pathogenic in avian species, as these determinants can otherwise prevent a virus from being grown in eggs.

A vaccine may include matrix protein, in order to benefit from the additional T cell epitopes that are located within this antigen. Thus a vaccine that includes haemagglutinin and neuraminidase may additionally include M1 and/or M2 matrix protein. Useful matrix fragments are disclosed in reference 71. Nucleoprotein may also be present.

Adjuvants

Vaccine compositions of the invention may include an adjuvant, which can function to enhance the immune responses (humoral and/or cellular) elicited in a patient who receives the composition. Vaccine adjuvants that can be used with the invention include, but are not limited to:

- A mineral-containing composition, including calcium salts and aluminum salts (or mixtures thereof). Calcium salts include calcium phosphate (e.g. the "CAP" particles disclosed in ref. 72). Aluminum salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt [73]. The adjuvants known as aluminum hydroxide and aluminum phosphate may be used. These names are conventional, but are used for convenience only, as neither is a precise description of the actual chemical compound which is present (e.g. see chapter 9 of reference 157). The invention can use any of the "hydroxide" or "phosphate" adjuvants that are in general use as adjuvants. The adjuvants known as "aluminium hydroxide" are typically aluminium oxyhydroxide salts, which are usually at least partially crystalline. The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. The invention can use a mixture of both an aluminium hydroxide and an aluminium phosphate. In this case there may be more aluminium phosphate than hydroxide e.g. a weight ratio of at least 2:1 e.g. ≥5:1, ≥6:1, ≥7:1, ≥8:1, ≥9:1, etc. The concentration of $Al^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml. A maximum of 0.85 mg/dose is preferred.
- Saponins [chapter 22 of ref. 157], which are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™. Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 74. Saponin formulations may also comprise a sterol, such as cholesterol[75]. Combinations of saponins and cholesterols can be used to form unique particles called immunostimulating complexes (ISCOMs) [chapter 23 of ref. 157]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 75-77. Optionally, the ISCOMS may be devoid of additional detergent [78]. A review of the development of saponin based adjuvants can be found in refs. 79 & 80.

Bacterial ADP-ribosylating toxins (e.g. the *E. coli* heat labile enterotoxin "LT", cholera toxin "CT", or pertussis toxin "PT"), and in particular detoxified derivatives thereof, such as the mutant toxins known as LT-K63 and LT-R72 [81] or CT-E29H [82]. The use of detoxified ADP-ribosylating toxins as mucosal adjuvants is described in ref. 83 and as parenteral adjuvants in ref. 84.

Bioadhesives and mucoadhesives, such as esterified hyaluronic acid microspheres [85] or chitosan and its derivatives [86].

Microparticles (i.e. a particle of ~100 nm to ~150 μm in diameter, more preferably ~200 nm to ~30 μm in diameter, or ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) being preferred, optionally treated to have a negatively-charged surface (e.g. with SDS) or a positively-charged surface (e.g. with a cationic detergent, such as CTAB).

Liposomes (Chapters 13 & 14 of ref. 157). Examples of liposome formulations suitable for use as adjuvants are described in refs. 87-89.

Muramyl peptides, such as N-acetylmuramyl-L-threonyl-D-isoglutamine ("thr-MDP"), N-acetyl-normuramyl-L-alanyl-D-isoglutamine (nor-MDP), N-acetyl-glucsaminyl-N-acetylmuramyl-L-AI-D-isoglu-L-Ala-dipalmitoxy propylamide ("DTP-DPP", or "Theramide™"), N-acetylmuramyl-L-alanyl-D-isoglutaminyl-L-alanine-2-(1'-2'dipalmitoyl-sn-glycero-3-hydroxyphosphoryloxy)-ethylamine ("MTP-PE").

A polyoxidonium polymer [90,91] or other N-oxidized polyethylene-piperazine derivative.

Methyl inosine 5'-monophosphate ("MIMP") [92].

A polyhydroxlated pyrrolizidine compound [93], such as one having formula:

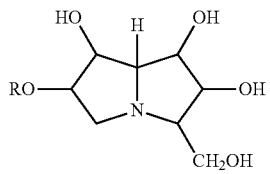

where R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepi-casuarine, etc.

A CD1d ligand, such as an α-glycosylceramide [94-101] (e.g. α-galactosylceramide), phytosphingosine-containing α-glycosylceramides, OCH, KRN7000 [(2S,3S,4R)-1-O-(α-D-galactopyranosyl)-2-(N-hexacosanoylamino)-1,3,4-octadecanetriol], CRONY-101, 3"-O-sulfo-galactosylceramide, etc.

A gamma inulin [102] or derivative thereof, such as algammulin.

An oil-in-water emulsion. Various such emulsions are known, and they typically include at least one oil and at least one surfactant, with the oil(s) and surfactant(s) being biodegradable (metabolisable) and biocompatible. Further details are given below.

An immunostimulatory oligonucleotide, such as one containing a CpG motif (a dinucleotide sequence containing an unmethylated cytosine residue linked by a phosphate bond to a guanosine residue), or a Cpl motif (a dinucleotide sequence containing cytosine linked to inosine), or a double-stranded RNA, or an oligonucleotide containing a palindromic sequence, or an oligonucleotide containing a poly(dG) sequence. Immunostimulatory oligonucleotides can include nucleotide modifications/analogs such as phosphorothioate modifications and can be double-stranded or (except for RNA) single-stranded. References 103, 104 and 105 disclose possible analog substitutions e.g. replacement of guanosine with 2'-deoxy-7-deazaguanosine. The adjuvant effect of CpG oligonucleotides is further discussed in refs. 106-111. The CpG sequence may be specific for inducing a Th1 immune response, such as a CpG-A ODN (oligodeoxynucleotide), or it may be more specific for inducing a B cell response, such a CpG-B ODN. CpG-A and CpG-B ODNs are discussed in refs. 113-115. Preferably, the CpG is a CpG-A ODN. Preferably, the CpG oligonucleotide is constructed so that the 5' end is accessible for receptor recognition. Optionally, two CpG oligonucleotide sequences may be attached at their 3' ends to form "immunomers". See, for example, references 112 & 116-118. A useful CpG adjuvant is CpG7909, also known as ProMune™ (Coley Pharmaceutical Group, Inc.). Another is CpG1826. As an alternative, or in addition, to using CpG sequences, TpG sequences can be used [119], and these oligonucleotides may be free from unmethylated CpG motifs. The immunostimulatory oligonucleotide may be pyrimidine-rich. For example, it may comprise more than one consecutive thymidine nucleotide ref. 119), and/or it may have a nucleotide composition with >25% thymidine (e.g. >35%, >40%, >50%, >60%, >80%, etc.). For example, it may comprise more than one consecutive cytosine nucleotide (ref. 119), and/or it may have a nucleotide composition with >25% cytosine (e.g. >35%, >40%, >50%, >60%, >80%, etc.). These oligonucleotides may be free from unmethylated CpG motifs. Immunostimulatory oligonucleotides will typically comprise at least 20 nucleotides. They may comprise fewer than 100 nucleotides.

A particularly useful adjuvant based around immunostimulatory oligonucleotides is known as IC31™ [120]. Thus an adjuvant used with the invention may comprise a mixture of (i) an oligonucleotide (e.g. between 15-40 nucleotides) including at least one (and preferably multiple) Cpl motifs, and (ii) a polycationic polymer, such as an oligopeptide (e.g. between 5-20 amino acids) including at least one (and preferably multiple) Lys-Arg-Lys tripeptide sequence(s).

3-O-deacylated monophosphoryl lipid A ('3dMPL', also known as 'MPLr™') [121-124]. In aqueous conditions, 3dMPL can form micellar aggregates or particles with different sizes e.g. with a diameter <150 nm or >500 nm. Either or both of these can be used with the invention, and the better particles can be selected by routine assay. Smaller particles (e.g. small enough to give a clear aqueous suspension of 3dMPL) are preferred for use according to the invention because of their superior activity [125]. Preferred particles have a mean diameter less than 220 nm, more preferably less than 200 nm or less than 150 nm or less than 120 nm, and can even have a mean diameter less than 100 nm. In most cases, however, the mean diameter will not be lower than 50 nm.

An imidazoquinoline compound, such as Imiquimod ("R-837") [126,127], Resiquimod ("R-848") [128], and their analogs; and salts thereof (e.g. the hydrochloride salts). Further details about immunostimulatory imidazoquinolines can be found in references 129 to 133.

A thiosemicarbazone compound, such as those disclosed in reference 134. Methods of formulating, manufacturing, and screening for active compounds are also described in reference 134. The thiosemicarbazones are particularly effective in the stimulation of human peripheral blood mononuclear cells for the production of cytokines, such as TNF-α.

A tryptanthrin compound, such as those disclosed in reference 135. Methods of formulating, manufacturing, and screening for active compounds are also described in reference 135. The thiosemicarbazones are particularly effective in the stimulation of human peripheral blood mononuclear cells for the production of cytokines, such as TNF-α.

A nucleoside analog, such as: (a) Isatorabine (ANA-245; 7-thia-8-oxoguanosine):

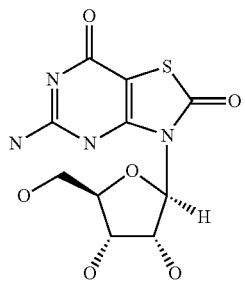 [SMILES: Nc1nc(=O)c2sc(=O)n([C@@H]3O[C@H](CO)[C@@H](O)[C@H]3O)c2[nH]1]

and prodrugs thereof; (b) ANA975; (c) ANA-025-1; (d) ANA380; (e) the compounds disclosed in references 136 to 138. Compounds containing lipids linked to a phosphate-containing acyclic backbone, such as the TLR4 antagonist E5564 [139, 140]:

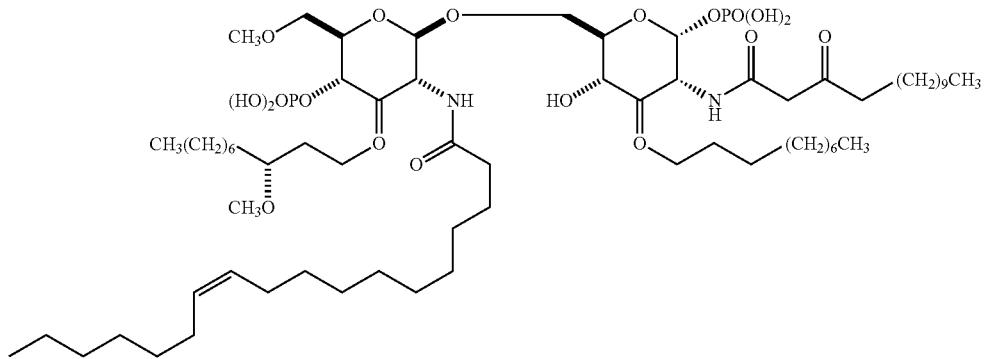

A substituted urea or compound of formula I, II or III, or a salt thereof:

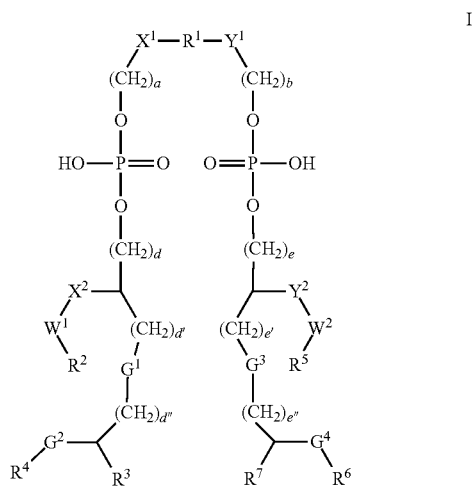

I

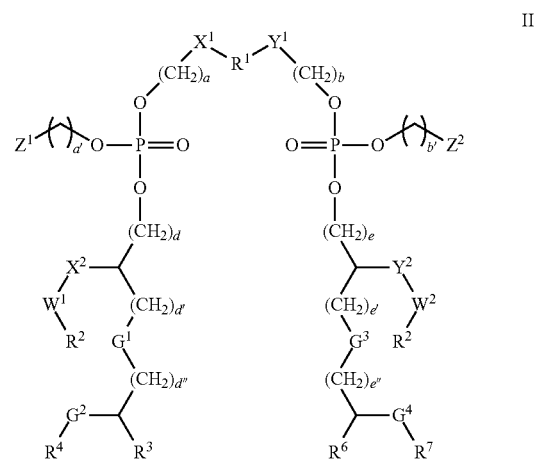

II

-continued

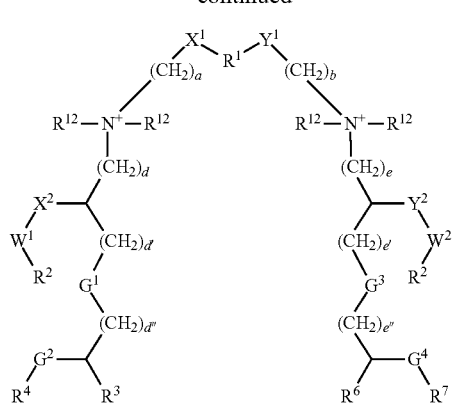

as defined in reference 141, such as 'ER 803058', 'ER 803732', 'ER 804053', ER 804058', 'ER 804059', 'ER 804442', 'ER 804680', 'ER 804764', ER 803022 or 'ER 804057' e.g.:

Derivatives of lipid A from *Escherichia coli* such as OM-174 (described in refs. 142 & 143).

Loxoribine (7-allyl-8-oxoguanosine) [144].

Compounds disclosed in reference 145, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds [146,147], Hydrapthalamide compounds, Benzophenone compounds, Isoxazole compounds, Sterol compounds, Quinazilinone compounds, Pyrrole compounds [148], Anthraquinone compounds, Quinoxaline compounds, Triazine compounds, Pyrazalopyrimidine compounds, and Benzazole compounds [149].

An aminoalkyl glucosaminide phosphate derivative, such as RC-529 [150,151].

A phosphazene, such as poly[di(carboxylatophenoxy)phosphazene]("PCPP") as described, for example, in references 152 and 153.

These and other adjuvant-active substances are discussed in more detail in references 157 & 158.

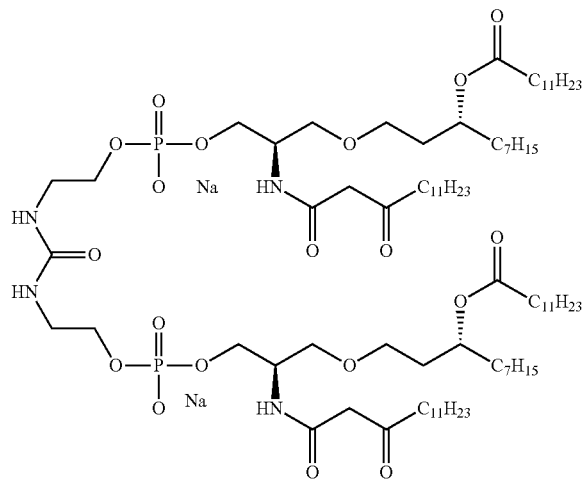

ER804057

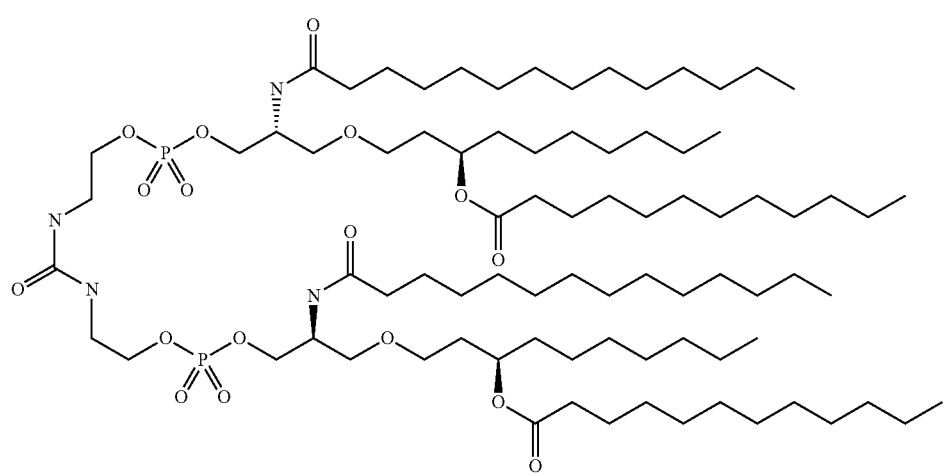

ER-803022

Compositions may include two or more of said adjuvants. Individual adjuvants may preferentially induce either a Th1 response or a Th2 response, and useful combinations of adjuvants can include both a Th2 adjuvant (e.g. an oil-in-water emulsion or an aluminium salt) and a Th1 adjuvant (e.g. 3dMPL, a saponin, or an immunostimulatory oligonucleotide). For example, compositions may advantageously comprise: both an aluminium salt and an immunostimulatory oligodeoxynucleotide; both an aluminium salt and a compound of formula I, II or III; both an oil-in-water emulsion and a compound of formula I, II or III; both an oil-in-water emulsion and an immunostimulatory oligodeoxynucleotide; both an aluminium salt and an α-glycosylceramide; both an oil-in-water emulsion and an α-glycosylceramide; both an oil-in-water emulsion and 3dMPL; both an oil-in-water emulsion and a saponin; etc. Mixtures of 3dMPL and oil-in-water emulsions are very useful.

Preferred adjuvants for use with the invention are oil-in-water emulsions, which have been found to be particularly suitable for use in adjuvanting influenza virus vaccines. Various such emulsions are known, and they typically include at least one oil and at least one surfactant, with the oil(s) and surfactant(s) being biodegradable (metabolisable) and biocompatible. The oil droplets in the emulsion are generally less than 5 μm in diameter, and ideally have a sub-micron diameter, with these small sizes being achieved with a microfluidiser to provide stable emulsions. Droplets with a size less than 220 nm are preferred as they can be subjected to filter sterilization.

The emulsion can comprise oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Other preferred oils are the tocopherols (see below). Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are Tween 80 (polyoxyethylene sorbitan monooleate), Span 85 (sorbitan trioleate), lecithin and Triton X-100.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Preferred emulsion adjuvants have an average droplets size of ≤1 μm e.g. ≤750 nm, ≤500 nm, ≤400 nm, ≤300 nm, ≤250 nm, ≤220 nm, ≤200 nm, or smaller. These droplet sizes can conveniently be achieved by techniques such as microfluidisation.

Specific oil-in-water emulsion adjuvants useful with the invention include, but are not limited to:

A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [154-156], as described in more detail in Chapter 10 of ref. 157 and chapter 12 of ref. 158. The MF59 emulsion advantageously includes citrate ions e.g. 10 mM sodium citrate buffer.

An emulsion of squalene, a tocopherol, and polysorbate 80 (Tween 80). The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene:tocopherol is preferably ≤1 as this provides a more stable emulsion. Squalene and Tween 80 may be present at a volume ratio of about 5:2 or at a weight ratio of about 11:5. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm. The emulsion may also include a 3-de-O-acylated monophosphoryl lipid A (3d-MPL). Another useful emulsion of this type may comprise, per human dose, 0.5-10 mg squalene, 0.5-11 mg tocopherol, and 0.1-4 mg polysorbate 80 [159].

An emulsion of squalene, a tocopherol, and a Triton detergent (e.g. Triton X-100). The emulsion may also include a 3d-MPL (see below). The emulsion may contain a phosphate buffer.

An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 g/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [160](0.05-1% Thr-MDP, 5% squalane, 2.5% Pluronic L121 and 0.2% polysorbate 80). It can also be used without the Thr-MDP, as in the "AF" adjuvant [161](5% squalane, 1.25% Pluronic L121 and 0.2% polysorbate 80). Microfluidisation is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [162]. The emulsion may also include one or more of: alditol; a cryoprotective agent (e.g. a sugar, such as dodecylmaltoside and/or sucrose); and/or an alkylpolyglycoside. The emulsion may include a TLR4 agonist [163]. Such emulsions may be lyophilized.

An emulsion of squalene, poloxamer 105 and Abil-Care [164]. The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; caprylic/capric triglyceride).

An emulsion having from 0.5-50% of an oil, 0.1-10% of a phospholipid, and 0.05-5% of a non-ionic surfactant. As described in reference 165, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in reference 166, produced by addition of aliphatic amine to desacylsaponin via the carboxyl group of glucuronic acid), dimethyidioctadecylammonium bromide and/or N,N-dioctadecyl-N,N-bis(2-hydroxyethyl)propanediamine.

An emulsion in which a saponin (e.g. QuilA or QS21) and a sterol (e.g. a cholesterol) are associated as helical micelles [167].

An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) [168].

An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) [168].

In some embodiments an emulsion may be mixed with antigen extemporaneously, at the time of delivery, and thus the adjuvant and antigen may be kept separately in a packaged or distributed vaccine, ready for final formulation at the time of use. In other embodiments an emulsion is mixed with antigen during manufacture, and thus the composition is packaged in a liquid adjuvanted form, as in the FLUAD™ product. The antigen will generally be in an aqueous form, such that the vaccine is finally prepared by mixing two liquids. The volume ratio of the two liquids for mixing can vary (e.g. between 5:1 and 1:5) but is generally about 1:1. Where concentrations of components are given in the above descriptions of specific emulsions, these concentrations are typically for an undiluted composition, and the concentration after mixing with an antigen solution will thus decrease.

An antigen and emulsion in a composition will typically be in admixture, although they may initially be presented in the form of a kit of separate components for extemporaneous admixing. Compositions will generally be in aqueous form when administered to a subject.

After the antigen and adjuvant have been mixed, haemagglutinin antigen will generally remain in aqueous solution but may distribute itself around the oil/water interface. In general, little if any haemagglutinin will enter the oil phase of the emulsion.

Where a composition includes a tocopherol, any of the α, β, γ, δ, ε or ξ tocopherols can be used, but α-tocopherols are preferred. The tocopherol can take several forms e.g. different salts and/or isomers. Salts include organic salts, such as succinate, acetate, nicotinate, etc. D-α-tocopherol and DL-α-tocopherol can both be used. Tocopherols are advantageously included in vaccines for use in elderly patients (e.g. aged 60 years or older) because vitamin E has been reported to have a positive effect on the immune response in this patient group [169]. They also have antioxidant properties that may help to stabilize the emulsions [170]. A preferred α-tocopherol is DL-α-tocopherol, and the preferred salt of this tocopherol is the succinate. The succinate salt has been found to cooperate with TNF-related ligands in vivo. Moreover, α-tocopherol succinate is known to be compatible with influenza vaccines and to be a useful preservative as an alternative to mercurial compounds [5].

Pharmaceutical Compositions

Compositions of the invention for administration to patients are pharmaceutically acceptable. They may include components in addition to the antigen e.g. they will typically include one or more pharmaceutical carrier(s) and/or excipient(s). A thorough discussion of such components is available in ref. 171.

A composition may include preservatives such as thiomersal or 2-phenoxyethanol. It is preferred, however, that the vaccine should be substantially free from (i.e. less than 5 μg/ml) mercurial material e.g. thiomersal-free [172,173]. Vaccines containing no mercury are more preferred, and α-tocopherol succinate can be included as an alternative to mercurial compounds [5]. Preservative-free vaccines are most preferred.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination [174], but keeping osmolality in this range is nevertheless preferred.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a composition will generally be between 5.0 and 8.1, and more typically between 6.0 and 8.0 e.g. 6.5 and 7.5, or between 7.0 and 7.8. A process of the invention may therefore include a step of adjusting the pH of the bulk vaccine prior to packaging.

The composition is preferably sterile. The composition is preferably non-pyrogenic e.g. containing <1 EU (endotoxin unit, a standard measure) per dose, and preferably <0.1 EU per dose. The composition is preferably gluten free.

The composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Influenza vaccines are typically administered in a dosage volume of about 0.5 ml, although a half dose (i.e. about 0.25 ml) may be administered to children according to the invention.

Compositions and kits are preferably stored at between 2° C. and 8° C. They should not be frozen. They should ideally be kept out of direct light.

If virus is grown on a cell line then it is standard practice to minimize the amount of residual cell line DNA in the final vaccine, in order to minimize any oncogenic activity of the DNA. Thus a vaccine composition prepared according to the invention preferably contains less than 10 ng (preferably less than 1 ng, and more preferably less than 100 pg) of residual host cell DNA per dose, although trace amounts of host cell DNA may be present.

Vaccines containing <10 ng (e.g. <1 ng, <100 pg) host cell DNA per 15 μg of haemagglutinin are preferred, as are vaccines containing <10 ng (e.g. <1 ng, <100 pg) host cell DNA per 0.25 ml volume. Vaccines containing <10 ng (e.g. <1 ng, <100 pg) host cell DNA per 50 μg of haemagglutinin are more preferred, as are vaccines containing <10 ng (e.g. <1 ng, <100 pg) host cell DNA per 0.5 ml volume.

It is preferred that the average length of any residual host cell DNA is less than 500 bp e.g. less than 400 bp, less than 300 bp, less than 200 bp, less than 100 bp, etc.

Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination is disclosed in references 175 & 14, involving a two-step treatment, first using a DNase (e.g. Benzonase), which may be used during viral growth, and then a cationic detergent (e.g. CTAB), which may be used during virion disruption. Removal by 3-propiolactone treatment can also be used [68].

Measurement of residual host cell DNA is now a routine regulatory requirement for biologicals and is within the normal capabilities of the skilled person. The assay used to measure DNA will typically be a validated assay [176,177]. The performance characteristics of a validated assay can be described in mathematical and quantifiable terms, and its possible sources of error will have been identified. The assay will generally have been tested for characteristics such as accuracy, precision, specificity. Once an assay has been calibrated (e.g. against known standard quantities of host cell DNA) and tested then quantitative DNA measurements can be routinely performed. Three main techniques for DNA quantification can be used: hybridization methods, such as Southern blots or slot blots [178]; immunoassay methods, such as the Threshold™ System [179]; and quantitative PCR [180]. These methods are all familiar to the skilled person, although the precise characteristics of each method may depend on the host cell in question e.g. the choice of probes for hybridization, the choice of primers and/or probes for amplification, etc. The Threshold™ system from Molecular Devices is a quantitative assay for picogram levels of total DNA, and has been used for monitoring levels of contaminating DNA in biopharmaceuticals [179]. A typical assay involves non-sequence-specific formation of a reaction complex between a biotinylated ssDNA binding protein, a urease-conjugated anti-ssDNA antibody, and DNA. All assay components are included in the complete Total DNA Assay Kit available from the manufacturer. Various commercial manufacturers offer quantitative PCR assays for detecting residual host cell DNA e.g. AppTec™ Laboratory Services, BioReliance™, Althea Technologies, etc. A comparison of a chemiluminescent hybridisation assay and the total DNA Threshold™ system for measuring host cell DNA contamination of a human viral vaccine can be found in reference 181.

Kits of the Invention

Vaccines may be prepared extemporaneously, at the time of delivery, particularly when an adjuvant is being used. Thus the invention provides kits including the various components ready for mixing. The kit allows the adjuvant and the antigen to be kept separately until the time of use. This arrangement can be useful when using an oil-in-water emulsion adjuvant.

The components are physically separate from each other within the kit, and this separation can be achieved in various ways. For instance, the two components may be in two separate containers, such as vials. The contents of the two vials can then be mixed e.g. by removing the contents of one vial and adding them to the other vial, or by separately removing the contents of both vials and mixing them in a third container.

In a preferred arrangement, one of the kit components is in a syringe and the other is in a container such as a vial. The syringe can be used (e.g. with a needle) to insert its contents into the second container for mixing, and the mixture can then be withdrawn into the syringe. The mixed contents of the syringe can then be administered to a patient, typically through a new sterile needle. Packing one component in a syringe eliminates the need for using a separate syringe for patient administration.

In another preferred arrangement, the two kit components are held together but separately in the same syringe e.g. a dual-chamber syringe, such as those disclosed in references 182-189 etc. When the syringe is actuated (e.g. during administration to a patient) then the contents of the two chambers are mixed. This arrangement avoids the need for a separate mixing step at the time of use.

The kit components will generally be in aqueous form. In some arrangements, a component (typically an antigen component rather than an adjuvant component) is in dry form (e.g. in a lyophilised form), with the other component being in aqueous form. The two components can be mixed in order to reactivate the dry component and give an aqueous composition for administration to a patient. A lyophilised component will typically be located within a vial rather than a syringe. Dried components may include stabilizers such as lactose, sucrose or mannitol, as well as mixtures thereof e.g. lactose/sucrose mixtures, sucrose/mannitol mixtures, etc. One possible arrangement uses an aqueous adjuvant component in a pre-filled syringe and a lyophilised antigen component in a vial.

Packaging of Compositions or Kit Components

Suitable containers for compositions of the invention (or kit components) include vials, syringes (e.g. disposable syringes), nasal sprays, etc. These containers should be sterile.

Where a composition/component is located in a vial, the vial is preferably made of a glass or plastic material. The vial is preferably sterilized before the composition is added to it. To avoid problems with latex-sensitive patients, vials are preferably sealed with a latex-free stopper, and the absence of latex in all packaging material is preferred. The vial may include a single dose of vaccine, or it may include more than one dose (a 'multidose' vial) e.g. 10 doses. Preferred vials are made of colorless glass.

A vial can have a cap (e.g. a Luer lock) adapted such that a pre-filled syringe can be inserted into the cap, the contents of the syringe can be expelled into the vial (e.g. to reconstitute lyophilised material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed. A vial may have a cap that permits aseptic removal of its contents, particularly for multidose vials.

Where a component is packaged into a syringe, the syringe may have a needle attached to it. If a needle is not attached, a separate needle may be supplied with the syringe for assembly and use. Such a needle may be sheathed. Safety needles are preferred. 1-inch 23-gauge, 1-inch 25-gauge and ⅝-inch 25-gauge needles are typical. Syringes may be provided with peel-off labels on which the lot number, influenza season and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield. Useful syringes are those marketed under the trade name "Tip-Lok"™.

Containers may be marked to show a half-dose volume e.g. to facilitate delivery to children. For instance, a syringe containing a 0.5 ml dose may have a mark showing a 0.25 ml volume.

Where a glass container (e.g. a syringe or a vial) is used, then it is preferred to use a container made from a borosilicate glass rather than from a soda lime glass.

A kit or composition may be packaged (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

Methods of Treatment, and Administration of the Vaccine

Vaccines of the invention are suitable for administration to human patients, and the invention provides a method of raising an immune response in a patient, comprising the step of administering a composition of the invention to the patient.

The invention also provides a kit or composition of the invention for use as a medicament. The invention also provides the medical uses discussed above.

These methods and uses will generally be used to generate an antibody response, preferably a protective antibody response. Methods for assessing antibody responses, neutralising capability and protection after influenza virus vaccination are well known in the art. Human studies have shown that antibody titers against hemagglutinin of human influenza virus are correlated with protection (a serum sample hemagglutination-inhibition titer of about 30-40 gives around 50% protection from infection by a homologous virus) [190]. Antibody responses are typically measured by hemagglutination inhibition, by microneutralisation, by single radial immunodiffusion (SRID), and/or by single radial hemolysis (SRH). These assay techniques are well known in the art.

Compositions of the invention can be administered in various ways. The most preferred immunisation route is by intramuscular injection (e.g. into the arm or leg), but other available routes include subcutaneous injection, intranasal [191-193], oral [194], intradermal [195,196], transcutaneous, transdermal [197], etc.

Vaccines of the invention may be used to treat both children and adults. Influenza vaccines are currently recommended for use in pediatric and adult immunisation, from the age of 6 months. Thus the patient may be less than 1 year old, 1-5 years old, 5-15 years old, 15-55 years old, or at least 55 years old. Preferred patients for receiving the vaccines are the elderly (e.g. ≥50 years old, ≥60 years old, preferably ≥65 years), the young (e.g. ≤5 years old), hospitalised patients, healthcare workers, armed service and military personnel, pregnant women, the chronically ill, immunodeficient patients, patients who have taken an antiviral compound (e.g. an oseltamivir or zanamivir compound; see below) in the 7 days prior to receiving the vaccine, people with egg allergies and people travelling abroad. The vaccines are not suitable solely for these groups, however, and may be used more generally in a population. For pandemic strains, administration to all age groups is preferred.

Preferred compositions of the invention will satisfy 1, 2 or 3 of the CPMP criteria for adult efficacy for each influenza strain, even though they are administered to children. These criteria are: (1) ≥70% seroprotection; (2) ≥40% seroconversion or significant increase; and/or (3) a GMT increase of ≥2.5-fold. In elderly (>60 years), these criteria are: (1) ≥60% seroprotection; (2)≥30% seroconversion; and/or (3) a GMT increase of ≥2-fold. These criteria are based on open label studies with at least 50 patients.

Treatment can be by a single dose schedule or a multiple dose schedule. In any particular influenza season (e.g. in a given 12 month period, typically in autumn or winter) a patient may thus receive a single dose of a composition of the invention or more than one dose (e.g. two doses). A single dose can raise a useful immune response against subtype H3N2 of influenza A virus, whereas two doses may be required to additionally provide a useful immune response against subtype H1N1 of influenza A virus and against influenza B virus. In a multiple dose schedule the various doses may be given by the same or different routes e.g. a parenteral prime and mucosal boost, a mucosal prime and parenteral boost, etc. Typically they will be given by the same route. Multiple doses will typically be administered at least 1 week apart (e.g. about 2 weeks, about 3 weeks, about 4 weeks, about 6 weeks, about 8 weeks, about 12 weeks, about 16 weeks, etc.). Giving two doses separated by from 25-30 days (e.g. 28 days) is particularly useful.

Vaccines produced by the invention may be administered to patients at substantially the same time as (e.g. during the same medical consultation or visit to a healthcare professional or vaccination centre) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a pneumococcal conjugate vaccine, etc.

Similarly, vaccines of the invention may be administered to patients at substantially the same time as (e.g. during the same medical consultation or visit to a healthcare professional) an antiviral compound, and in particular an antiviral compound active against influenza virus (e.g. oseltamivir and/or zanamivir). These antivirals include neuraminidase inhibitors, such as a (3R,4R,5S)-4-acetylamino-5-amino-3 (1-ethylpropoxy)-1-cyclohexene-1-carboxylic acid or 5-(acetylamino)-4-[(aminoiminomethyl)-amino]-2,6-anhydro-3,4,5-trideoxy-D-glycero-D-galactonon-2-enonic acid, including esters thereof (e.g. the ethyl esters) and salts thereof (e.g. the phosphate salts). A preferred antiviral is (3R,4R,5S)-4-acetylamino-5-amino-3(1-ethylpropoxy)-1-cyclohexene-1-carboxylic acid, ethyl ester, phosphate (1:1), also known as oseltamivir phosphate (TAMIFLU™).

Combined Aspects of the Invention

As discussed above, the invention provides a number of improvements to existing processes for preparing vaccine antigens from disintegrated influenza viruses. As well as being used separately, these improvements can be used in combination. Disrupted virions obtained by processes including such combinations can be used for the preparation of influenza vaccines.

Thus, for example, the invention provides a process for preparing disrupted influenza virions, comprising steps of: (i) obtaining a composition comprising influenza virions in the absence of detergent and, preferably, in the presence of a phosphate buffer; (ii) inactivating the influenza virions in the absence of detergent and, preferably, in the presence of a phosphate buffer; (iii) splitting the inactivated virions with a reagent comprising a first detergent in a buffer (preferably a phosphate buffer) having an ionic strength of 100 mM or greater; and (iv) exchanging the first detergent for a second detergent.

The material obtained after detergent exchange can be further purified, including the use of ultrafiltration through a cellulose ultrafiltration membrane (according to the fourth aspect).

Similarly, the invention provides a process for preparing disrupted influenza virions, comprising steps of: (i) obtaining a liquid medium containing influenza virions; (ii) optionally concentrating the medium; (iii) diafiltering the liquid medium to provide a virion-containing retentate including a low conductivity buffer; (iv) capturing virions from the retentate by a process selected from affinity capture, pseudo-affinity capture, chromatography or adsorption; (v) inactivating the influenza virions in the absence of detergent and, preferably, in the presence of a phosphate buffer; (vi) splitting the inactivated virions with a reagent comprising a first detergent in a buffer (preferably a phosphate buffer) having an ionic strength of 100 mM or greater; and (vii) exchanging the first detergent for a second detergent. The material can, as above, be further purified.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encaphalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

Where a cell substrate is used for reassortment or reverse genetics procedures, it is preferably one that has been approved for use in human vaccine production e.g. as in Ph Eur general chapter 5.2.3.

MODES FOR CARRYING OUT THE INVENTION

A H5N1 strain of influenza A virus was successfully grown on MDCK cells. An initial attempt to prepare purified surface glycoproteins from this strain used a process that had previously been used successfully with a H1N1 strain, but the process performed very badly. More than 95% of viral HA had been lost after the CTAB-based splitting step, and the step used to remove CTAB also removed more than 75% of HA. Furthermore, the final HA was antigenically damaged and much of it was not detectable by SRID. Thus the H1N1 process was modified.

Virus growth and harvest were not changed. After harvest, however, ultrafiltration was used to concentrate the virions 5-fold (hollow-fiber PES membrane, 500 kDa cut-off), and the concentrated virion suspension was then diafiltered into a 10 mM phosphate buffer (pH 7.0±0.1). Virions were purified (concentrated) using a CS resin (equilibrated in the same 10 mM phosphate buffer). In a further ultrafiltration/diafiltration step a new buffer was used. Rather than use a Tris buffer, as in the H1N1 process, a phosphate buffer was used (buffer 'A': 50 mM phosphate, pH 7.5) for equilibration and diafiltration. Moreover, unlike the H1N1 process this buffer did not include polysorbate 80.

Purified virions were then inactivated using β-propiolactone. Unlike the H1N1 process, however, the β-propiolactone was prepared in buffer 'A'.

Inactivated virions were then split using CTAB, but again the CTAB was prepared in buffer 'A'. Moreover, rather than performing splitting in a low concentration of Tris buffer, it was performed in 200 mM NaCl with 50 mM phosphate, pH 7.5. Thus the ionic strength and buffer system used during splitting were both changed.

Ultracentrifugation was used to prepare surface antigens in the same way as the H1N1 process, but a subsequent step of CTAB removal (by adsorption) was altered. Whereas the CTAB adsorbent in the H1N1 process was equilibrated in a Tris buffer, for H5N1 it was equilibrated in buffer 'A', supplemented by 2.5 g/L of polysorbate 80. Addition of polysorbate 80 at this stage substituted for the pre-inactivation addition of polysorbate 80 in the H1N1 process.

Subsequent purification steps were the same, except again that Tris buffers were replaced by buffer 'A', and that the final ultrafiltration membrane was changed to reduce hydrophobicity and to decrease its size exclusion limit, with a hydrophilic cellulose acetate membrane with low intrinsic protein adsorption characteristics being selected.

Figure 1:
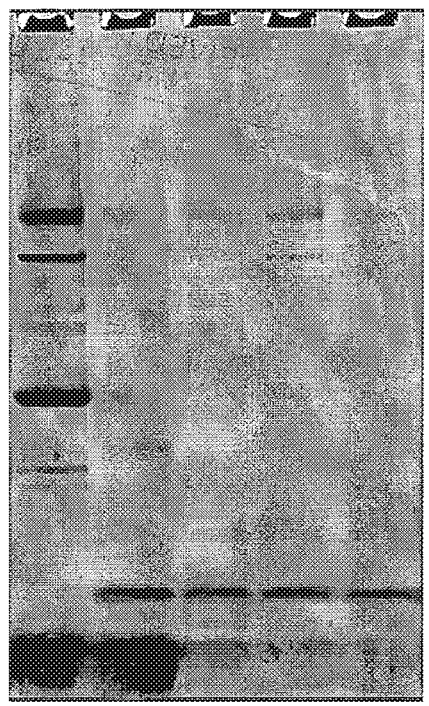
FIGS. 1 and 2 both show SDS-PAGE analysis of five stages during antigen purification. The five lanes, from left to right, show proteins present at the following stages: (i) after 1-propiolactone inactivation; (ii) after CTAB splitting; (iii) after 15 hours of CTAB removal by adsorption; (iv) after adsorption is complete; and (v) after post-adsorption sterile filtration.
Figure 2:
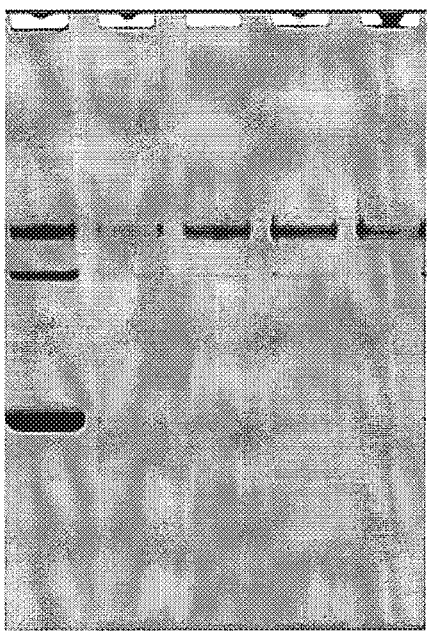

FIGS. 1 and 2 show the effects of these changes on antigen purification. Whereas in FIG. 1, which shows the results of using the H1N1 process on the H5N1 virus, the amount of HA antigen is vastly decreased after splitting, the same drop is not seen in FIG. 2. Moreover, high levels of HA remain present during the subsequent purification steps.

Whereas the H1N1 process gave a final HA concentration of <10 μg/mL when performed on the H5N1 virus, the modified process provided a final concentration of 505 μg/mL i.e. a >50-fold improvement. Total HA recovery, as measured by SRID, was assessed as 36%. HA purity was very good. Residual CTAB concentration was <0.05 μg per μg of HA.

The same process is also useful for treating other influenza A viruses e.g. H1N1 strains. A modified process is also useful, in which polysorbate 80 is added after the CS chromatography step but prior to splitting, or after splitting but before CTAB removal. If the amount of polysorbate 80 added in either of these steps was less than 1.5 g/L then further polysorbate 80 is added in the subsequent purification steps, but prior to the final ultrafiltration.

It will be understood that the invention has been described by way of example only and modifications may be made whilst remaining within the scope and spirit of the invention.

REFERENCES (THE CONTENTS OF WHICH ARE HEREBY INCORPORATED BY REFERENCE)

[1] Vaccines. (eds. Plotkin & Orenstein). 4th edition, 2004, ISBN: 0-7216-9688-0.
[2] WO02/067983.
[3] WO02/074336.
[4] WO01/21151.
[5] WO02/28422.
[6] Gross et al. (1981) J Clin Microbiol 14:534-8.
[7] WO02/097072.
[8] WO2005/113756.
[9] U.S. Pat. No. 4,140,762.
[10] U.S. Pat. No. 4,327,182.
[11] U.S. Pat. No. 4,158,054.
[12] U.S. Pat. No. 4,064,232.
[13] U.S. Pat. No. 6,048,537.
[14] U.S. Pat. No. 5,948,410.
[15] Lina et al. (2000) Biologicals 28:95-103.
[16] Gross et al. (1983)Am J Dis Child. 137:26-8.
[17] Tannock et al. (1991) Biologicals 19:17-21.
[18] U.S. Pat. No. 5,522,991.
[19] U.S. Pat. No. 4,253,963.
[20] U.S. Pat. No. 5,505,890.
[21] Opitz et al. (2007) Vaccine 25:939-47.
[22] Wallis et al. (1972) Appl Environ Microbiol 23:740-4.
[23] Mizutani (1963) Nature 198:109-10.
[24] Lapidus (1969) Appl Microbiol 17:504-6.
[25] Rota et al. (1992) J Gen Virol 73:2737-42.
[26] GenBank sequence GI:325176.
[27] Herlocher et al. (2004) J Infect Dis 190(9): 1627-30.
[28] Le et al. (2005) Nature 437(7062): 1108.
[29] Hoffmann et al. (2002) Vaccine 20:3165-3170.
[30] Subbarao et al. (2003) Virology 305:192-200.
[31] Liu et al. (2003) Virology 314:580-590.
[32] Ozaki et al. (2004) J. Virol. 78:1851-1857.
[33] Webby et al. (2004) Lancet 363:1099-1103.
[34] WO00/60050.
[35] WO01/04333.
[36] U.S. Pat. No. 6,649,372.
[37] Neumann et al. (2005) Proc Natl Acad Sci USA 102:16825-9.
[38] WO2007/124327
[39] Wang & Duke (2007) Virology J 4:102
[40] WO2006/067211.
[41] WO01/83794.
[42] Hoffmann et al. (2000) Virology 267(2):310-7.
[43] Kistner et al. (1998) Vaccine 16:960-8.
[44] Kistner et al. (1999) Dev Biol Stand 98:101-110.
[45] Bruhl et al. (2000) Vaccine 19:1149-58.
[46] Pau et al. (2001) Vaccine 19:2716-21.
[47] http://www.atcc.org/
[48] http://locus.umdnj.edu/
[49] WO03/076601.
[50] WO2005/042728.
[51] WO03/043415.
[52] WO01/85938.
[53] WO2006/108846.
[54] WO97/37000.
[55] Brands et al. (1999) Dev Biol Stand 98:93-100.
[56] Halperin et al. (2002) Vaccine 20:1240-7.
[57] Tree et al. (2001) Vaccine 19:3444-50.
[58] EP-A-1260581 (WO01/64846).
[59] WO2006/071563.
[60] WO2005/113758.
[61] WO97/37001.

[62] WO2006/027698.
[63] Stanley (1944) *J Exp Med* 79:255-66.
[64] Reimer et al. (1966) *J Bacteriol* 92:1271-2.
[65] Reimer et al. (1966) *Science* 152:1379-81.
[66] Sokolov et al. (1971) *Arch Virol* 35:356-63.
[67] Heyward et al. (1977) *Arch Virol* 55:107-19.
[68] WO2007/052163.
[69] Treanor et al. (1996) *J Infect Dis* 173:1467-70.
[70] Keitel et al. (1996) *Clin Diagn Lab Immunol* 3:507-10.
[71] WO2007/085969.
[72] U.S. Pat. No. 6,355,271.
[73] WO00/23105.
[74] U.S. Pat. No. 5,057,540.
[75] WO96/33739.
[76] EP-A-0109942.
[77] WO96/11711.
[78] WO00/07621.
[79] Barr et al. (1998) *Advanced Drug Delivery Reviews* 32:247-271.
[80] Sjolanderet et al. (1998) *Advanced Drug Delivery Reviews* 32:321-338.
[81] Pizza et al. (2000) *Int J Med Microbiol* 290:455-461.
[82] Tebbey et al. (2000) *Vaccine* 18:2723-34.
[83] WO95/17211.
[84] WO98/42375.
[85] Singh et all (2001) *J Cont Release* 70:267-276.
[86] WO99/27960.
[87] U.S. Pat. No. 6,090,406
[88] U.S. Pat. No. 5,916,588
[89] EP-A-0626169.
[90] Dyakonova et al. (2004) *Int Immunopharmacol* 4(13): 1615-23.
[91] FR-2859633.
[92] Signorelli & Hadden (2003) *Int Immunopharmacol* 3(8): 1177-86.
[93] WO2004/064715.
[94] De Libero et al, *Nature Reviews Immunology*, 2005, 5: 485-496
[95] U.S. Pat. No. 5,936,076.
[96] Oki et al, *J. Clin. Investig.*, 113: 1631-1640
[97] US2005/0192248
[98] Yang et al, *Angew. Chem. Int. Ed.*, 2004, 43: 3818-3822
[99] WO2005/102049
[100] Goff et al, *J. Am. Chem., Soc.*, 2004, 126: 13602-13603
[101] WO03/105769
[102] Cooper (1995) *Pharm Biotechnol* 6:559-80.
[103] Kandimalla et al. (2003) *Nucleic Acids Research* 31:2393-2400.
[104] WO02/26757.
[105] WO99/62923.
[106] Krieg (2003) *Nature Medicine* 9:831-835.
[107] McCluskie et al. (2002) *FEMS Immunology and Medical Microbiology* 32:179-185.
[108] WO98/40100.
[109] U.S. Pat. No. 6,207,646.
[110] U.S. Pat. No. 6,239,116.
[111] U.S. Pat. No. 6,429,199.
[112] Kandimalla et al. (2003) *Biochemical Society Transactions* 31 (part 3):654-658.
[113] Blackwell et al. (2003) *J Immunol* 170:4061-4068.
[114] Krieg (2002) *Trends Immunol* 23:64-65.
[115] WO01/95935.
[116] Kandimalla et al. (2003) *BBRC* 306:948-953.
[117] Bhagat et al. (2003) *BBRC* 300:853-861.
[118] WO03/035836.
[119] WO01/22972.
[120] Schellack et al. (2006) *Vaccine* 24:5461-72.
[121] Myers et al. (1990) pages 145-156 of *Cellular and molecular aspects of endotoxin reactions.*
[122] Ulrich (2000) Chapter 16 (pages 273-282) of reference 158.
[123] Johnson et al. (1999) *J Med Chem* 42:4640-9.
[124] Baldrick et al. (2002) *Regulatory Toxicol Pharmacol* 35:398-413.
[125] WO 94/21292.
[126] U.S. Pat. No. 4,680,338.
[127] U.S. Pat. No. 4,988,815.
[128] WO92/15582.
[129] Stanley (2002) *Clin Exp Dermatol* 27:571-577.
[130] Wu et al. (2004) *Antiviral Res.* 64(2):79-83.
[131] Vasilakos et al. (2000) *Cell Immunol.* 204(1):64-74.
[132] U.S. Pat. Nos. 4,689,338, 4,929,624, 5,238,944, 5,266,575, 5,268,376, 5,346,905, 5,352,784, 5,389,640, 5,395,937, 5,482,936, 5,494,916, 5,525,612, 6,083,505, 6,440,992, 6,627,640, 6,656,938, 6,660,735, 6,660,747, 6,664,260, 6,664,264, 6,664,265, 6,667,312, 6,670,372, 6,677,347, 6,677,348, 6,677,349, 6,683,088, 6,703,402, 6,743,920, 6,800,624, 6,809,203, 6,888,000 and 6,924,293.
[133] Jones (2003) *Curr Opin Investig Drugs* 4:214-218.
[134] WO2004/060308.
[135] WO2004/064759.
[136] U.S. Pat. No. 6,924,271.
[137] US2005/0070556.
[138] U.S. Pat. No. 5,658,731.
[139] Wong et al. (2003) *J Clin Pharmacol* 43(7):735-42.
[140] US2005/0215517.
[141] WO03/011223.
[142] Meraldi et al. (2003) *Vaccine* 21:2485-2491.
[143] Pajak et al. (2003) *Vaccine* 21:836-842.
[144] U.S. Pat. No. 5,011,828.
[145] WO2004/87153.
[146] U.S. Pat. No. 6,605,617.
[147] WO02/18383.
[148] WO2004/018455.
[149] WO03/082272.
[150] Johnson et al. (1999) *Bioorg Med Chem Lett* 9:2273-2278.
[151] Evans et al. (2003) *Expert Rev Vaccines* 2:219-229.
[152] Andrianov et al. (1998) *Biomaterials* 19:109-115.
[153] Payne et al. (1998) *Adv Drug Delivery Review* 31:185-196.
[154] WO90/14837.
[155] Podda & Del Giudice (2003) *Expert Rev Vaccines* 2:197-203.
[156] Podda (2001) *Vaccine* 19: 2673-2680.
[157] *Vaccine Design: The Subunit and Adjuvant Approach* (eds. Powell & Newman) Plenum Press 1995 (ISBN 0-306-44867-X).
[158] *Vaccine Adjuvants: Preparation Methods and Research Protocols* (Volume 42 of *Methods in Molecular Medicine* series). ISBN: 1-59259-083-7. Ed. O'Hagan.
[159] WO2008/043774.
[160] Allison & Byars (1992) *Res Immunol* 143:519-25.
[161] Hariharan el al. (1995) *Cancer Res* 55:3486-9.
[162] US-2007/014805.
[163] US-2007/0191314.
[164] Suli et al. (2004) *Vaccine* 22(25-26):3464-9.
[165] WO95/11700.
[166] U.S. Pat. No. 6,080,725.
[167] WO2005/097181.
[168] WO2006/113373.

[169] Han et al. (2005) *Impact of Vitamin E on Immune Function and Infectious Diseases in the Aged at Nutrition, Immune functions and Health* EuroConference, Paris, 9-10 Jun. 2005.
[170] U.S. Pat. No. 6,630,161.
[171] Gennaro (2000) *Remington: The Science and Practice of Pharmacy*. 20th edition, ISBN: 0683306472.
[172] Banzhoff (2000) *Immunology Letters* 71:91-96.
[173] WO02/097072.
[174] Nony et al. (2001) *Vaccine* 27:3645-51.
[175] EP-B-0870508.
[176] Lundblad (2001) *Biotechnology and Applied Biochemistry* 34:195-197.
[177] *Guidance for Industry: Bioanalytical Method Validation*. U.S. Department of Health and Human Services Food and Drug Administration Center for Drug Evaluation and Research (CDER) Center for Veterinary Medicine (CVM). May 2001.
[178] Ji et al. (2002) *Biotechniques*. 32:1162-7.
[179] Briggs (1991) *J Parenter Sci Technol.* 45:7-12.
[180] Lahijani et al. (1998) *Hum Gene Ther.* 9:1173-80.
[181] Lokteff et al. (2001) *Biologicals*. 29:123-32.
[182] WO2005/089837.
[183] U.S. Pat. No. 6,692,468.
[184] WO00/07647.
[185] WO99/17820.
[186] U.S. Pat. No. 5,971,953.
[187] U.S. Pat. No. 4,060,082.
[188] EP-A-0520618.
[189] WO98/01174.
[190] Potter & Oxford (1979) *Br Med Bull* 35: 69-75.
[191] Greenbaum et al. (2004) *Vaccine* 22:2566-77.
[192] Zurbriggen et al. (2003) *Expert Rev Vaccines* 2:295-304.
[193] Piascik (2003) *J Am Pharm Assoc* (Wash D.C.). 43:728-30.
[194] Mann et al. (2004) *Vaccine* 22:2425-9.
[195] Halperin et al. (1979) *Am J Public Health* 69:1247-50.
[196] Herbert et al. (1979). Infect Dis 140:234-8.
[197] Chen et al. (2003) *Vaccine* 21:2830-6.

The invention claimed is:

1. A method for disrupting influenza virions, the method comprising steps of:
   (i) obtaining a composition comprising influenza virions prepared from a cell culture,
   (ii) inactivating the influenza virions to obtain inactivated virions, and
   (iii) splitting the inactivated virions in the presence of a buffer having an ionic strength of from 200 mM to 800 mM, wherein the buffer comprises phosphate.

2. The method of claim 1, wherein the influenza virions are from an influenza A virus.

3. The method of claim 1, wherein the influenza virions are from an influenza A virus of H5 hemagglutinin subtype.

4. The method of claim 1, wherein the cell culture is a mammalian cell culture or an avian cell culture.

5. A method for manufacturing an influenza vaccine, the method comprising steps of:
   carrying out the method of claim 1,
   obtaining a bulk antigen preparation from the disrupted virions of step (iii), and
   formulating the bulk antigen preparation into an influenza vaccine.

6. The method of claim 5, wherein the influenza virions are from an influenza A virus.

7. The method of claim 5, wherein the influenza virions are from an influenza A virus of H5 hemagglutinin subtype.

8. The method of claim 5, wherein the cell culture is a mammalian cell culture or an avian cell culture.

9. The method of claim 5, wherein the influenza vaccine contains less than 10 ng host cell DNA.

10. The method of claim 5, wherein the influenza vaccine is a monovalent or trivalent influenza vaccine.

11. The method of claim 5, wherein the influenza vaccine comprises hemagglutinin from at least one B strain.

12. The method of claim 5, wherein the influenza vaccine comprises from about 3.75 µg to about 15 µg hemagglutinin, per strain, per dose.

13. The method of claim 5, wherein the step of formulating comprises combining the bulk antigen preparation with an adjuvant.

14. The method of claim 13, wherein the adjuvant is an oil-in-water emulsion.

15. The method of claim 1, wherein the buffer has an ionic strength of at least 300 mM.

16. The method of claim 1, wherein the buffer has an ionic strength of at least 400 mM.

17. The method of claim 1, wherein the buffer has an ionic strength of at least 500 mM.

18. The method of claim 1, wherein the buffer has a pH of from 6.5 to 8.5.

19. The method of claim 1, wherein the buffer has a pH of from 7.0 to 8.0.

20. The method of claim 1, wherein the buffer has a pH of from 7.0 to 7.8.

21. The method of claim 1, wherein the method results in a higher than 20-fold increase in antigen yield, when compared to a method for disrupting influenza virions comprising corresponding steps (i)-(iii), except that step (iii) is performed in the presence of a Tris buffer.

22. The method of claim 1, wherein the method results in an increased antigen yield, when compared to a method for disrupting influenza virions comprising corresponding steps (i)-(iii), except that the buffer in step (iii) has an ionic strength of less than 200 mM.

* * * * *